United States Patent
Xu et al.

[11] Patent Number: 5,796,482
[45] Date of Patent: Aug. 18, 1998

[54] APPARATUS/METHOD FOR OPTICAL MEASURING A PHYSICAL AMOUNT OF A SPECIFIC COMPONENT CONTAINED IN A SUBSTANCE

[75] Inventors: Kexin Xu; Michio Naka; Norihito Suzuki, all of Kyoto, Japan

[73] Assignee: Kyoto Daiichi Kagaku Co., Ltd., Kyoto-fu, Japan

[21] Appl. No.: 741,261

[22] Filed: Oct. 30, 1996

[30] Foreign Application Priority Data

Oct. 31, 1995 [JP] Japan .................. 7-319442

[51] Int. Cl.$^6$ .................................. G01B 9/02
[52] U.S. Cl. .......................... 356/349; 356/345
[58] Field of Search ............... 356/349, 345, 356/346

[56] References Cited

U.S. PATENT DOCUMENTS

| | | | |
|---|---|---|---|
| 4,451,782 | 5/1984 | Ashida | 324/76.26 |
| 4,565,449 | 1/1986 | Grego | 356/349 |
| 5,325,172 | 6/1994 | Kataoka et al. | 356/349 |
| 5,428,447 | 6/1995 | Toida | 356/349 |

*Primary Examiner*—Frank G. Font
*Assistant Examiner*—Jason D Vierra-Eisenberg
*Attorney, Agent, or Firm*—Kinney & Lange, P.A.

[57] ABSTRACT

The optical measuring apparatus of this invention for measuring a physical amount of a specific component contained in a substance to be measured by the use of measurement light which passes through the substance to be measured and the use of predetermined reference light includes: a first interfering polarizing plate for obtaining a first light interference signal by interfering the measurement light; a second interfering polarizing plate for obtaining a second light interference signal by interfering the reference light; a first photoelectric converting section for converting the first light interference signal into a first electric signal; a second photoelectric converting section for converting the second light interference signal into a second electric signal; a first phase expanding section for expanding a phase of the first electric signal; a second phase expanding section for expanding a phase of the second electric signal; a phase difference measuring section for measuring a phase difference between a phase expanded by the first phase expanding section and a phase expanded by the second phase expanding section; and a physical amount determining section for determining the physical amount of the specific component contained in the substance to be measured depending on the phase difference measured by the phase difference measuring section.

4 Claims, 5 Drawing Sheets

Vm

Vr

Vm1"

Vr1"

5,796,482

APPARATUS/METHOD FOR OPTICAL MEASURING A PHYSICAL AMOUNT OF A SPECIFIC COMPONENT CONTAINED IN A SUBSTANCE

BACKGROUND OF THE INVENTION

1. Field of the Invention

The present invention relates to an optical measuring apparatus for measuring the physical amount of a specific component contained in a substance to be measured, and a method employed by such an apparatus.

2. Description of the Related Art

A method for measuring a physical amount by use of light interference is known. The physical amounts include, for example, the displacement of an object, the surface profile of an object, the birefringence of a substance having the birefringence property, and the concentration of an aqueous solution of a substance having a rotatory power.

The method utilizes the fact that a relationship exists between the phase of heterodyning interference light and the physical amount of a specific component which is an object of the measurement. The method includes converting the interference light into an electric signal and determining the physical amount of the specific component by measuring the phase of the electric signal. In general, the physical amount is determined by measuring a shift in the phase of the measurement light from the phase of a known reference light (i.e., the phase difference between the reference light and the measurement light).

In general, the phase difference between the reference light and the measurement light is affected by the change in the physical amount to be measured. As the change in the physical amount becomes larger, the phase difference becomes larger. The phase difference is normally extremely small, however. A phase difference meter with extremely high precision is therefore required to measure the change in the physical amount with high resolution and high precision.

The limit of the resolution of a phase difference meter is generally 0.1° to 0.01° electrically. A phase difference below the above limit cannot be measured. It is not possible, therefore, to measure a minute change in the physical amount by the conventional method.

SUMMARY OF THE INVENTION

The optical measuring apparatus of this invention for measuring a physical amount of a specific component contained in a substance to be measured by the use of measurement light which passes through the substance to be measured and the use of predetermined reference light includes: a first interfering means for obtaining a first light interference signal by interfering the measurement light; a second interfering means for obtaining a second light interference signal by interfering the reference light; a first photoelectric converting section for converting the first light interference signal into a first electric signal; a second photoelectric converting section for converting the second light interference signal into a second electric signal; a first phase expanding section for expanding a phase of the first electric signal; a second phase expanding section for expanding a phase of the second electric signal; a phase difference measuring section for measuring a phase difference between a phase expanded by the first phase expanding section and a phase expanded by the second phase expanding section; and a physical amount determining section for determining the physical amount of the specific component contained in the substance to be measured depending on the phase difference measured by the phase difference measuring section.

In one embodiment of the invention, the reference light passes through a reference substance.

In another embodiment of the invention, the first phase expanding section includes at least one first multiplying circuit for multiplying the first electric signal, and the second phase expanding section includes at least one second multiplying circuit for multiplying the second electric signal.

In still another embodiment of the invention, the first multiplying circuit includes a first multiplier for expanding a frequency and a phase of the first electric signal, a first amplifier for amplifying an output of the first multiplier, and a first waveform processor for extracting a signal having a predetermined frequency from an output of the first amplifier to remove noise, and the second multiplying circuit includes a second multiplier for expanding a frequency and a phase of the second electric signal, the second amplifier for amplifying an output of the second multiplier, and a second waveform processor for extracting a signal having a predetermined frequency from an output of the second amplifier to remove noise.

According to another aspect of the invention, an optical measuring method for measuring a physical amount of a specific component contained in a substance to be measured by the use of measurement light which passes through the substance to be measured and the use of predetermined reference light is provided. The method includes the steps of: a) obtaining a first light interference signal by interfering the measurement light; b) obtaining a second light interference signal by interfering the reference light; c) converting the first light interference signal into a first electric signal; d) converting the second light interference signal into a second electric signal; e) expanding a phase of the first electric signal; f) expanding a phase of the second electric signal; g) measuring a phase difference between a phase expanded at step e) and a phase expanded at step f); and h) determining the physical amount of the specific component contained in the substance to be measured depending on the phase difference measured at step g).

In one embodiment of the invention, the reference light passes through a reference substance.

In another embodiment of the invention, the step e) comprises the step of: i) multiplying the first electric signal at least once, and the step f) comprises the step of: j) multiplying the second electric signal at least once.

In still another embodiment of the invention, the step i) comprises the steps of: expanding a frequency and a phase of the first electric signal by use of a first multiplier; amplifying an output of the first multiplier by use of a first amplifier; and extracting a signal having a predetermined frequency from an output of the first amplifier to remove noise, and the step j) comprises the steps of: expanding a frequency and a phase of the second electric signal by use of a second multiplier; amplifying an output of the second multiplier by use of a second amplifier; and extracting a signal having a predetermined frequency from an output of the second amplifier to remove noise.

Thus, the invention described herein makes possible the advantages of (1) providing an optical measuring apparatus with an improved measuring precision capable of measuring a minute change in a physical amount, and (2) providing an optical measuring method employed by such an apparatus.

These and other advantages of the present invention will become apparent to those skilled in the art upon reading and

3 understanding the following detailed description with reference to the accompanying figures.

DESCRIPTION OF THE PREFERRED EMBODIMENTS

The present invention will be described by way of example with reference to the accompanying drawings.

Figure 1:
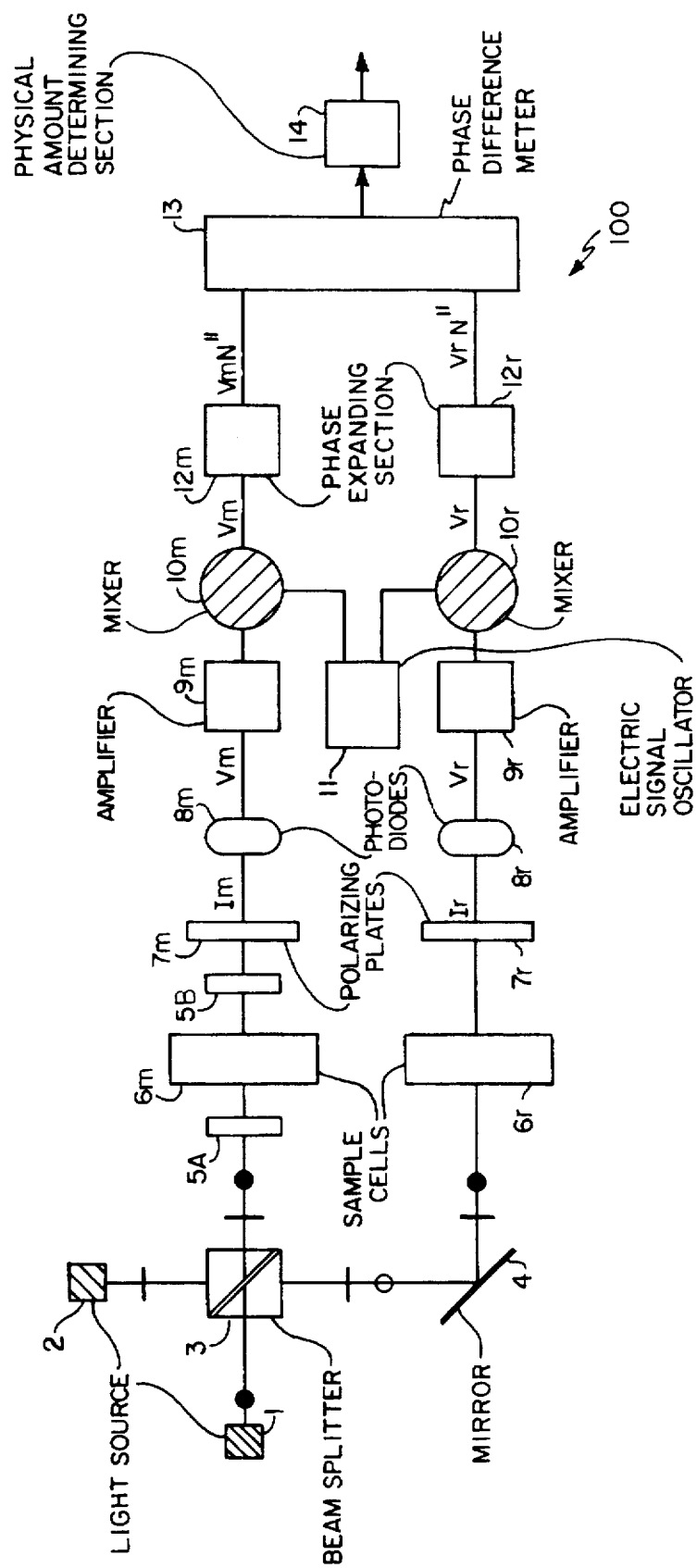
FIG. 1 illustrates a configuration of an optical measuring apparatus according to the present invention.

FIG. 1 illustrates a configuration of an optical measuring apparatus 100 according to the present invention. The optical measuring apparatus 100 includes light sources 1 and 2, a beam splitter 3, a mirror 4, sample cells 6m and 6r, polarizing plates 7m and 7r, photodiodes 8m and 8r, amplifiers 9m and 9r, mixers 10m and 10r, an electric signal oscillator 11, phase expanding sections 12m and 12r, a phase difference meter 13, and a physical amount determining section 14.

The light sources 1 and 2 emit beams of light. A beam emitted from the light source 1 and a beam emitted from the light source 2 have frequencies different from each other, and are polarized in directions apart from each other by 90°. For example, the light source 1 emits a beam with a frequency $f_0$ polarized in the horizontal direction, while the light source 2 emits a beam with a frequency $f_0+\Delta f$ polarized in the vertical direction. The beams emitted from the light sources 1 and 2 are incident on the beam splitter 3.

The beam splitter 3 splits the beams from the light sources 1 and 2 into measurement light and reference light. The resultant measurement light and reference light respectively include a horizontally linearly polarized light component with a frequency $f_0$ and a vertically linearly polarized light component with a frequency $f_0+\Delta f$. These linearly polarized light components are coherent components.

The sample cell 6m, the polarizing plate 7m, and the photodiode 8m are disposed on the optical path for the measurement light output from the beam splitter 3. The measurement light passes through the sample cell 6m which stores a substance to be measured. The measurement light then passes through the polarizing plate 7m, where the horizontally linearly polarized light component and the vertically linearly polarized light component are superimposed on each other to interfere with each other. As a result, a light interference signal $I_m$ with a frequency $\Delta f$ and a phase $\Phi_m$ is obtained as the output of the polarizing plate 7m. The phase $\Phi_m$ depends both on the phase difference between the horizontally linearly polarized light component and the

4 vertically linearly polarized light component and a phase difference caused by the nature of the substance to be measured.

The light interference signal $I_m$ is represented by expression (1) below:

$$I_m = A_m \cdot \operatorname{Sin}|\omega t + \Phi_m| \quad (1)$$

wherein $A_m$ denotes the amplitude of the light interference signal $I_m$, $\omega$ denotes the frequency of interference beat, and $\Phi_m$ denotes the phase of the light interference signal $I_m$.

If the substance to be measured has a rotatory power, ¼ wave plates 5A and 5B are additionally disposed on the optical path for the measurement light as shown in FIG. 1.

In general, when a linearly polarized light component passes through a birefringence plate such as the ¼ wave plate 5A or 5B, the polarizing state of the beam changes. In the case where the ¼ wave plate is disposed so that the axis thereof is 45° with respect to the plane of vibration of the linearly polarized light component, the linearly polarized light component is converted into a circularly polarized light component by the ¼ wave plate. In reverse, a circularly polarized light component is converted into a linearly polarized light component by the ¼ wave plate.

By passing through the ¼ wave plate 5A, the horizontally linearly polarized light component and the vertically linearly polarized light component included in the measurement light output from the beam splitter 3 are converted into a clockwise circularly polarized light component and a counterclockwise circularly polarized light component, respectively. Then, the measurement light passes through the sample cell 6m. When the substance to be measured has a rotatory power, the phases of the clockwise circularly polarized light component and counterclockwise circularly polarized light component shift from each other. The clockwise circularly polarized light component and the counterclockwise circularly polarized light component then pass through the ¼ wave plate 5B to be converted back into the horizontally linearly polarized light component and the vertically linearly polarized light component, respectively. The measurement light then passes through the polarizing plate 7m.

The reference light output from the beam splitter 3 is reflected by the mirror 4, changing the direction by 90°. The sample cell 6r, the polarizing plate 7r, and the photodiode 8r are disposed on the optical path for the reference light reflected by the mirror 4.

The reference light output from the beam splitter 3 passes through the sample cell 6r which stores no substance to be measured. Then, the reference light passes through the polarizing plate 7r, where the horizontally linearly polarized light component and the vertically linearly polarized light component are superimposed with each other to interfere each other. As a result, a light interference signal $I_r$ with a frequency $\Delta f$ and a phase $\Phi_r$ is obtained as an output of the polarizing plate 7r. The phase $\Phi_r$ depends on the phase difference between the horizontally linearly polarized light component and the vertically linearly polarized light component.

The light interference signal $I_r$ is represented by expression (2) below:

$$I_r = A_r \cdot \operatorname{Sin}|\omega t + \Phi_r| \quad (2)$$

wherein $A_r$ denotes the amplitude of the light interference signal $I_r$, $\omega$ denotes the frequency of interference beat, and $\Phi_r$ denotes the phase of the light interference signal $I_r$.

The photodiode 8m converts the light interference signal $I_m$ into an electric signal $V_m$, while the photodiode 8r converts the light interference signal $I_r$ into an electric signal $V_r$.

The electric signals $V_m$ and $V_r$ are represented by expressions (3) and (4) below, respectively:

$$V_m = B_m \cdot \text{Sin} [\omega t + \Phi_m] \quad (3)$$

$$V_r = B_r \cdot \text{Sin} [\omega t + \Phi_r] \quad (4)$$

wherein $B_m$ and $B_r$ denote the amplitude of the electric signals $V_m$ and $V_r$, respectively.

Accordingly, the phase difference $\Delta\Phi$ between the electric signals $V_m$ and $V_r$ is represented by expression (5) below:

$$\Delta\Phi = \Phi_m - \Phi_r \quad (5)$$

The electric signal $V_m$ is amplified by the amplifier 9m and then mixed with an oscillated electric signal output from the electric signal oscillator 11 by the mixer 10m so as to obtain a frequency range measurable by the phase difference meter 13. The output of the mixer 10m is supplied to the phase expanding section 12m. Likewise, the electric signal $V_r$ is supplied to the phase expanding section 12r via the amplifier 9r and the mixer 10r.

Figure 2:
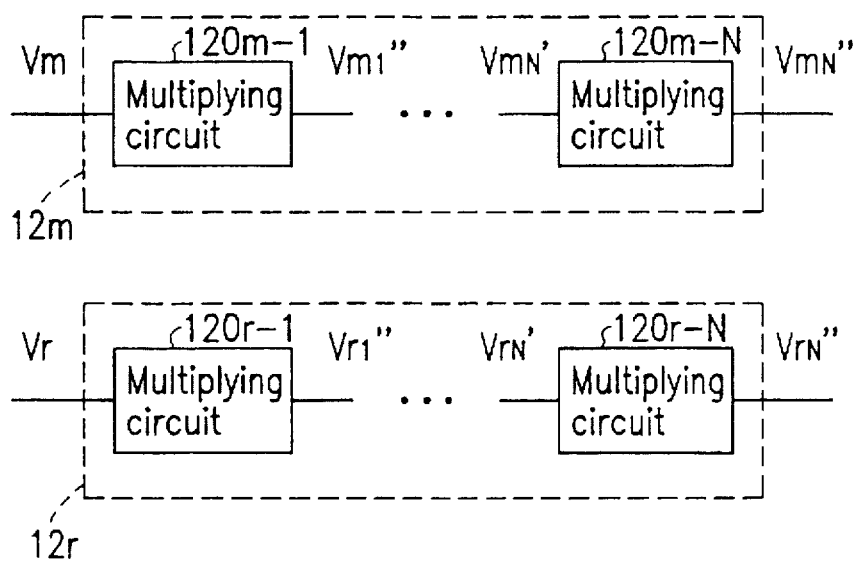
FIG. 2 illustrates configurations of phase expanding sections for measurement light and reference light of the apparatus.

FIG. 2 illustrates configurations of the phase expanding sections 12m and 12r. The phase expanding section 12m includes N multiplying circuits 120m-1 to 120m-N which are connected in series. The phase expanding section 12r includes N multiplying circuits 120r-1 to 120r-N which are connected in series.

Figure 3:
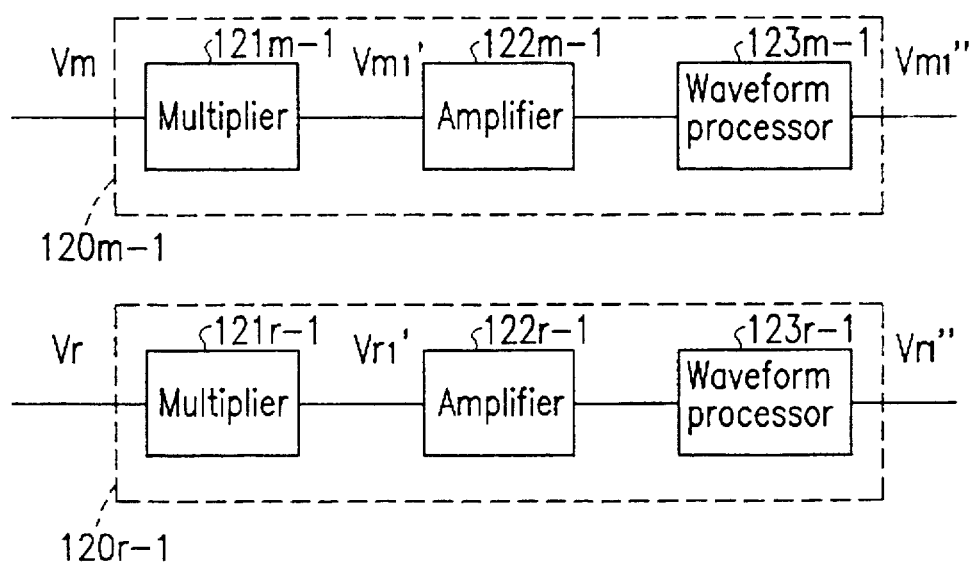
FIG. 3 illustrates configurations of multiplying circuits for measurement light and reference light of the phase expanding sections of the apparatus.

FIG. 3 illustrates configurations of the multiplying circuits 120m-1 and 120r-1. The multiplying circuit 120m-1 includes a multiplier 121m-1, an amplifier 122m-1, and a waveform processor 123m-1. The multiplying circuit 120r-1 includes a multiplier 121r-1, an amplifier 122r-1, and a waveform processor 123r-1.

The multiplier 121m-1 multiplies the electric signal $V_m$ output from the mixer 10m by itself so as to expand the frequecncy and the phase of the electric signal $V_m$. As a result, an electric signal $V_{m1}'$ is obtained.

The electric signal $V_{m1}'$ is represented by expression (6) below:

$$\begin{aligned} V_{m1}' &= V_m * V_m \\ &= B_m \cdot \text{Sin}[\omega t + \Phi_m] * B_m \cdot \text{Sin}[\omega t + \Phi_m] \\ &= B_m^2/2 [1 - \text{Cos}(2\omega t + 2\Phi_m)] \\ &= D_m [1 - \text{Cos}(2\omega t + \Psi_m)] \end{aligned} \quad (6)$$

wherein $D_m$ denotes the amplitude of the electric signal $V_{m1}'$ and $\Psi_m$ denotes the phase of the electric signal $V_{m1}'$.

Likewise, the multiplier 121r-1 multiplies the electric signal $V_r$ output from the mixer 10r by itself so as to expand the frequency and the phase of the electric signal $V_r$. As a result, an electric signal $V_{r1}'$ is obtained.

The electric signal $V_{r1}'$ is represented by expression (6) below:

$$\begin{aligned} V_{r1}' &= V_r * V_r \\ &= B_r \cdot \text{Sin}[\omega t + \Phi_r] * B_r \cdot \text{Sin}[\omega t + \Phi_r] \\ &= B_r^2/2 [1 - \text{Cos}(2\omega t + 2\Phi_r)] \\ &= D_r [1 - \text{Cos}(2\omega t + \Psi_r)] \end{aligned} \quad (7)$$

wherein $D_r$ denotes the amplitude of the electric signal $V_{r1}'$ and $\Psi_r$ denotes the phase of the electric signal $V_{r1}'$.

Accordingly, the phase difference $\Delta\Psi$ between the electric signals $V_{m1}'$ and $V_{r1}'$ is represented by expression (8) below:

$$\Delta\Psi = \Psi_m - \Psi_r = 2\Delta\Phi \quad (8)$$

The amplifier 122m-1 amplifies the electric signal output from the multiplier 121m-1 so that the amplitude of the signal attenuated by the frequency expansion processing by the multiplier 121m-1 is compensated to resume the original amplitude.

The waveform processor 123m-1 extracts a required frequency from the electric signal to remove noise and outputs an electric signal $V_{m1}''$.

The electric signal $V_{m1}''$ is represented by expression (9) below:

$$V_{m1}'' = D_{m1} \cdot \text{Cos}(2\omega t + 2\Phi_m) \quad (9)$$

It is found from expressions (3) and (9) that the phase of the electric signal $V_{m1}''$ has been expanded to double that of the electric signal $V_m$.

The electric signal $V_{m1}''$ is output from the multiplying circuit 120m-1. The configurations of the multiplying circuits 120m-2 to 120m-N are the same as that of the multiplying circuit 120m-1. An electric signal $V_{mN}''$ output from the multiplying circuit 120m-N is therefore represented by expression (10) below:

$$V_{mN}'' = D_{mN} \cdot \text{Cos}(2^N \omega t + 2^N \Phi_m) \quad (10)$$

It is found from expressions (3) and (10) that the phase of the electric signal $V_{mN}''$ has been expanded $2^N$ times the phase of the electric signal $V_m$.

Likewise, an electric signal $V_{rN}''$ output from the multiplying circuit 120r-N is represented by expression (11) below:

$$V_{rN}'' = D_{rN} \cdot \text{Cos}(2^N \omega t + 2^N \Phi_r) \quad (11)$$

It is found from expressions (4) and (11) that the phase of the electric signal $V_{rN}''$ has been expanded $2^N$ times the phase of the electric signal $V_r$.

Accordingly, the phase difference $\Delta\Psi_N$ between the electric signal $V_{mN}''$ output from the phase expanding section 12m and the electric signal $V_{rN}''$ output from the phase expanding section 12r is represented by expression (12) below:

$$\Delta\Psi_N = 2^N \Phi_m - 2^N \Phi_r = 2^N \Delta\Phi \quad (12)$$

The phase difference $\Delta\Psi_N$ is measured by the phase difference meter 13. The phase difference $\Delta\Psi_N$ and the physical amount of a specific component contained in the substance to be measured has a predetermined relationship. For example, the physical amount of the specific component is defined as a function F of the phase difference $\Delta\Psi_N$. The function F is given.

The physical amount determining section 14 determines the physical amount based on the phase difference $\Delta\Psi_N$. The physical amounts include, for example, the displacement of an object, the surface profile of an object, the birefringence of a substance having the birefringence property, and the concentration of an aqueous solution of a substance having a rotatory power.

Thus, by repeating the multiplication by N times in the phase expanding sections 12m and 12r, electric signals with a phase difference expanded by $2^N$ times from the phase difference $\Delta\Phi$ which is directly related to the physical amount ($\Delta\Psi_N = 2^N \Delta\Phi$) is obtained. This allows a specific physical amount of a substance to be measured with higher precision by use of a phase difference meter with a conventional precision.

The effect of the phase expansion by the multiplying circuit 120m-1 shown in FIG. 3 was examined using an AC electric signal with a reduced frequency of 1 MHz obtained from 2-channel light heterodyning interference.

Figure 4:
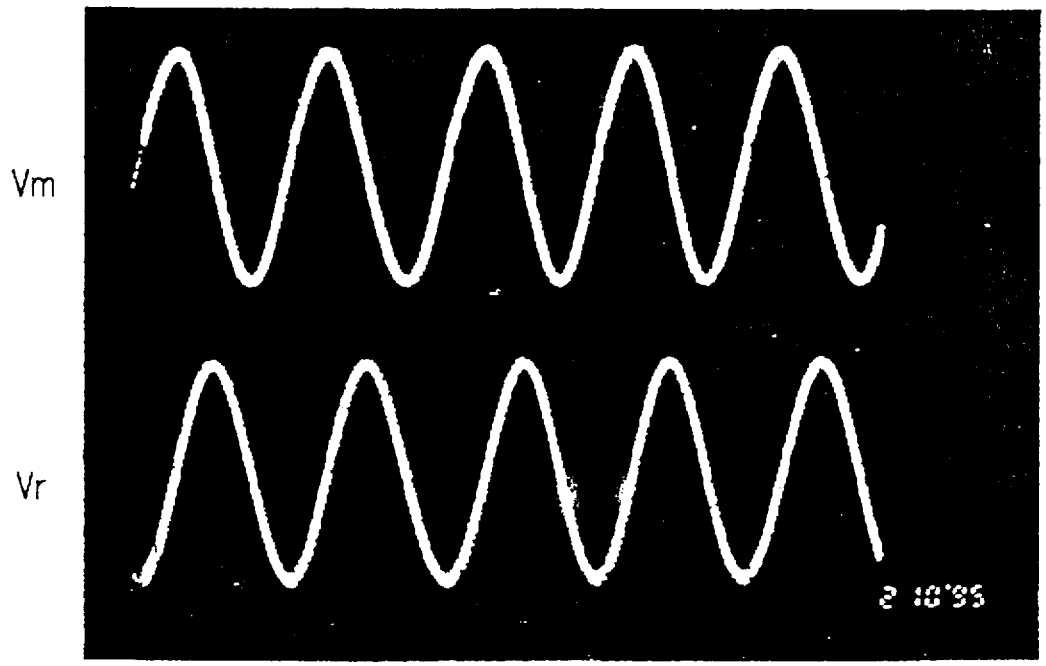
FIG. 4 illustrates waveforms of signals input into the multiplying circuits for measurement light and reference light.

FIG. 4 shows waveforms of the electric signal $V_m$ corresponding to the measurement light and the electric signal $V_r$ corresponding to the reference light both obtained before the phase expansion by the multiplying circuit 120m-1 and 120r-1. These waveforms can be observed by use of an oscilloscope.

Figure 5:
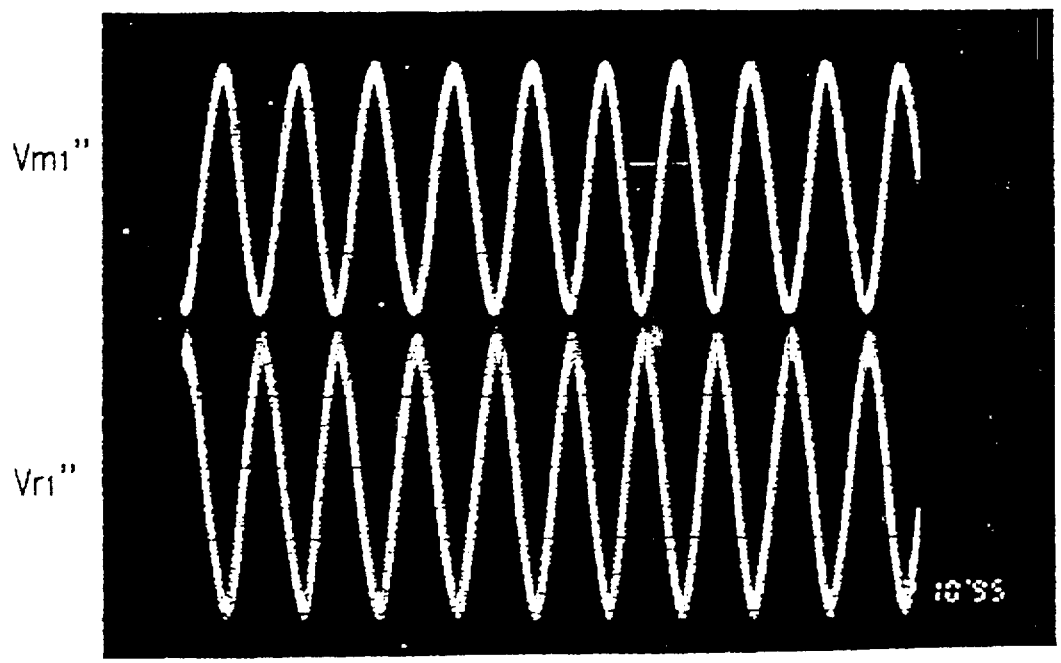
FIG. 5 illustrates waveforms of signals output from the multiplying circuits for measurement light and reference light.

FIG. 5 shows waveforms of the electric signal $V_{m1}$" corresponding to the measurement light and the electric signal $V_{r1}$" corresponding to the reference light both obtained after the phase expansion by the multiplying circuit 120m-1 and 120r-1. These waveforms can be observed by use of an oscilloscope.

It is observed from FIGS. 4 and 5 that the frequencies of the electric signals are doubled by the processing by the multiplying circuits 120m-1 and 120r-1.

Moreover, while the phase difference between the electric signal $V_m$ corresponding to the measurement light and the electric signal $V_r$ corresponding to the reference light is 90° in FIG. 4, the phase difference between the electric signal $V_{m1}$" corresponding to the measurement light and the electric signal $V_{r1}$" corresponding to the reference light has been expanded to 180° in FIG. 5.

Figure 6:
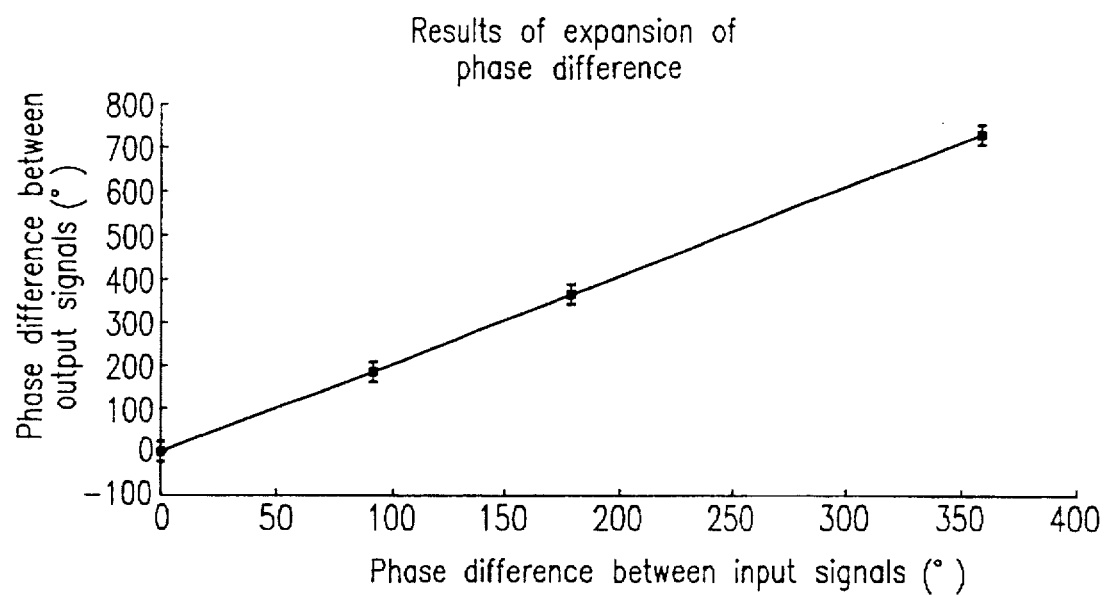
FIG. 6 is a graph showing the relationship between the phase difference between the signals input into the phase expanding sections and the phase difference between the output signals output from the phase expanding sections.

FIG. 6 shows the relationship between the phase difference between the signals input into the phase expanding sections 12m and 12r and the phase difference between the signals output from the phase expanding sections 12m and 12r. It is found from FIG. 6 that the phase difference has been expanded by the phase expanding sections 12m and 12r.

Incidentally, the sample cell 6r may store a reference substance to allow the reference light to pass through the reference substance. The reference substance may be the air, for example. Alternatively, the inside of the sample cell 6r may be vacuum.

Mixers may be used as the multipliers. Filters such as a band-pass filter and a high-pass filter may be used as the waveform processors.

In the multiplying circuit, a mixer may be used to decrease the frequency of the electric signal after the increase of the frequency by the multiplier. This facilitates the measurement of the phase difference.

Thus, according to the optical measuring apparatus and method of the present invention, the phase of a first electric signal corresponding to the measurement light and that of a second electric signal corresponding to the reference light are expanded. This expands the phase difference between the first electric signal and the second electric signal. By expanding the phase difference, the precision of the measurement of the phase difference improves. Since the phase difference and the physical amount are in a predetermined relationship, the precision of the measurement of the physical amount also improves.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An optical measuring apparatus for measuring a physical amount of a specific component contained in a substance to be measured by the use of measurement light which passes through the substance to be measured and the use of predetermined reference light, the optical measuring apparatus comprising:

a first interfering means for obtaining a first light interference signal by interfering the measurement light;

a second interfering means for obtaining a second light interference signal by interfering the reference light;

a first photoelectric converting section for converting the first light interference signal into a first electric signal;

a second photoelectric converting section for converting the second light interference signal into a second electric signal;

a first phase expanding section for expanding a phase of the first electric signal, the first phase expanding section including at least one first multiplying circuit for multiplying the first electric signal, the first multiplying circuit including a first multiplier for expanding a frequency and a phase of the first electric signal, a first amplifier for amplifying an output of the first multiplier, and a first waveform processor for extracting a signal having a predetermined frequency from an output of the first amplifier to remove noise;

a second phase expanding section for expanding a phase of the second electric signal, the second phase expanding section including at least one second multiplying circuit for multiplying the second electric signal, the second multiplying circuit including a second multiplier for expanding a frequency and a phase of the second electric signal, a second amplifier for amplifying an output of the second multiplier, and a second waveform processor for extracting a signal having a predetermined frequency from an output of the second amplifier to remove noise;

a phase difference measuring section for measuring a phase difference between a phase expanded by the first phase expanding section and a phase expanded by the second phase expanding section; and a physical amount determining section for determining the physical amount of the specific component contained in the substance to be measured depending on the phase difference measured by the phase difference measuring section.

2. An optical measuring apparatus according to claim 1, wherein the reference light passes through a reference substance.

3. An optical measuring method for measuring a physical amount of a specific component contained in a substance to be measured by the use of measurement light which passes through the substance to be measured and the use of predetermined reference light, the method comprising the steps of:

a) obtaining a first light interference signal by interfering the measurement light;

b) obtaining a second light interference signal by interfering the reference light;

c) converting the first light interference signal into a first electric signal;

d) converting the second light interference signal into a second electric signal;

e) expanding a phase of the first electric signal comprising the steps of:

e1) multiplying the first electric signal at least once, including expanding a frequency and a phase of the first electric signal by use of a first multiplier; amplifying an output of the first multiplier by use of a first amplifier; and extracting a signal having a predetermined frequency from an output of the first amplifier to remove noise, and e2) multiplying the second electric signal at least once, including expanding a frequency and a phase of the second electric signal by use of a second multiplier; amplifying an output of the second multiplier by use of a second amplifier; and extracting a signal having a predetermined frequency from an output of the second amplifier to remove noise;

f) expanding a phase of the second electric signal;

g) measuring a phase difference between a phase expanded at step e) and a phase expanded at step f); and h) determining the physical amount of the specific component contained in the substance to be measured depending on the phase difference measured at step g).

4. An optical measuring method according to claim 3, wherein the reference light passes through a reference substance.

* * * * *